(12) United States Patent
Shibahara (10) Patent No.: US 8,728,988 B2
(45) Date of Patent: May 20, 2014

(54) PROBE ARRAY BASE, METHOD FOR MANUFACTURING PROBE ARRAY BASE, METHOD FOR MANUFACTURING PROBE ARRAY

(75) Inventor: Teruhisa Shibahara, Kyoto (JP)

(73) Assignee: Murata Manufacturing Co., Ltd., Nagaokakyo-Shi, Kyoto-fu (JP)

( * ) Notice: Subject to any disclaimer, the term of this patent is extended or adjusted under 35 U.S.C. 154(b) by 0 days.

(21) Appl. No.: 13/487,605

(22) Filed: Jun. 4, 2012

(65) Prior Publication Data

US 2012/0238474 A1 Sep. 20, 2012

Related U.S. Application Data

(60) Division of application No. 12/168,294, filed on Jul. 7, 2008, now abandoned, which is a continuation of application No. PCT/JP2006/325518, filed on Dec. 21, 2006.

(30) Foreign Application Priority Data

Jan. 10, 2006 (JP) .................................. 2006-002736

(51) Int. Cl.
*C40B 60/00* (2006.01)
(52) U.S. Cl.
USPC ................. 506/33; 506/13; 422/50; 422/552
(58) Field of Classification Search
None
See application file for complete search history.

(56) References Cited

U.S. PATENT DOCUMENTS

| | | | |
|---|---|---|---|
| 4,146,365 A | 3/1979 | Kay et al. | |
| 4,977,078 A | 12/1990 | Niimura et al. | |
| 6,720,157 B2 | 4/2004 | Indermuhle et al. | |
| 2001/0036669 A1 | 11/2001 | Jedrzejewski et al. | |
| 2002/0160536 A1 | 10/2002 | Regnier et al. | |
| 2004/0077107 A1* | 4/2004 | Vogeli | 438/1 |
| 2004/0142491 A1 | 7/2004 | Indermuhle et al. | |
| 2005/0035983 A1 | 2/2005 | Cruchon-Dupeyrat et al. | |

FOREIGN PATENT DOCUMENTS

| | | |
|---|---|---|
| JP | 2001-83163 | 3/2001 |
| JP | 2001-343385 | 12/2001 |
| JP | 2003-524193 | 8/2003 |
| JP | 2004-004076 A | 1/2004 |
| JP | 2004-045055 A | 2/2004 |
| JP | 2004-160368 | 6/2004 |
| JP | 2005-17153 | 1/2005 |
| WO | WO-02/078834 A2 | 10/2002 |
| WO | WO-03/042697 A1 | 5/2003 |
| WO | WO-03/046508 A2 | 6/2003 |
| WO | WO-03/059518 A1 | 7/2003 |
| WO | WO-2007/080761 A1 | 7/2007 |

OTHER PUBLICATIONS

Corning Transwell Permeable Supports Selection and Use Guide (public availability date Apr. 13, 2005).*
PCT/JP2006/325518, International Search Report dated Jan. 30, 2007.
PCT/JP2006/325518, Written Opinion dated Jan. 30, 2007.

* cited by examiner

*Primary Examiner* — Christopher M Gross
(74) *Attorney, Agent, or Firm* — Dickstein Shapiro LLP (57) ABSTRACT

A probe array base including probe-holding portions which are periodically arranged on a solid base member and which have grooves is prepared by anisotropically etching a single-crystalline silicon substrate. Probe solutions are supplied to the probe-holding portions by capillary action from a plurality of tank arrays having a certain cylinder period. This allows a probe array to be completed. The probe array is used as, for example, a DNA or antigen chip, has a high degree of integration, and is capable of holding a constant and sufficient number of probe molecules.

7 Claims, 12 Drawing Sheets

PROBE ARRAY BASE, METHOD FOR MANUFACTURING PROBE ARRAY BASE, METHOD FOR MANUFACTURING PROBE ARRAY

CROSS REFERENCE TO RELATED APPLICATIONS

The present application is a divisional of application Ser. No. 12/168,294, filed Jul. 7, 2008, which is a continuation of International Application No. PCT/JP2006/325518, filed Dec. 21, 2006, which claims priority to Japanese Patent Application No. JP2006-002736, filed Jan. 10, 2006, the entire contents of each of these applications being incorporated herein by reference in their entirety.

FIELD OF THE INVENTION

The present invention relates to a probe array base used in a chemical and a biochemical field, a method for manufacturing the probe array base, and a method for manufacturing a probe array in which a probe solution is held by the probe-holding portions of the probe array base.

BACKGROUND OF THE INVENTION

DNA chips are tools for simultaneous multiple genetic analyses, simultaneous investigations of the presence of various types of mRNAs, or simultaneous multiple analyses of SNPs (single nucleotide polymorphisms) and are attracting much attention. A DNA chip is a probe array including periodically arranged probe-holding portions holding different types of probes including known DNAs hybridizing with target DNA or RNA molecules.

Antigen chips and antibody chips are also tools for simultaneous investigations of the presence of various types of antibodies and antigens and are attracting much attention. An antigen chip is a probe array including periodically arranged probe-holding portions holding different types of probes including known antigens binding to target antibody molecules. An antibody chip is a probe array including periodically arranged probe-holding portions holding different types of probes including known antibodies binding to target antigen molecules.

Figure 15:
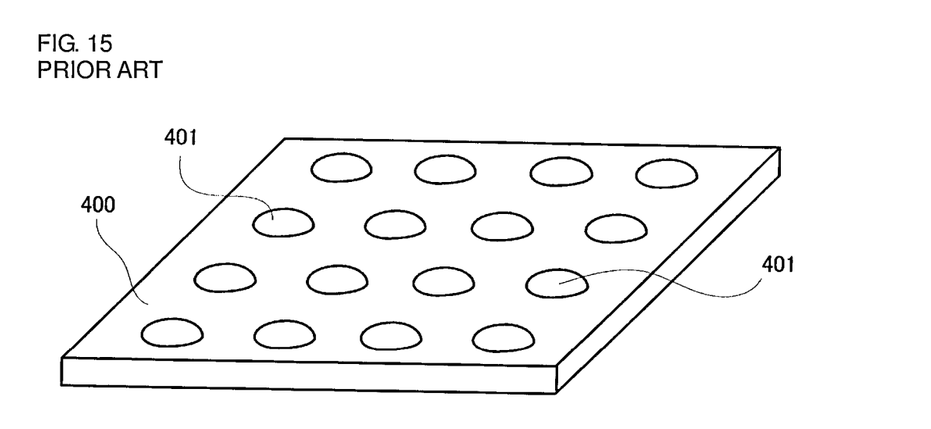
FIG. 15 is an illustration showing a probe array manufactured by a conventional spotting method.

A known method for manufacturing an ordinary probe array is as follows: a probe solution is trickled onto a base such as a glass slide such that probe spots are arranged on the base. Such a method is referred to as a spotting method. FIG. 15 shows a probe array, manufactured by the spotting method, including a glass slide 400 on which spots 401 of a probe solution are arranged. The spotted solution is finally dried such that probe molecules are adsorbed on the glass slide 400, whereby this probe array is obtained. Known examples of the spotting method include methods for discharging probe solutions from syringes, micropipettes, or ink jet nozzles onto bases and methods for providing probe solutions onto bases by bringing needles carrying these probe solutions into contact with these bases.

Patent Document 1 discloses a micropipette used to densely arrange micro-sized droplets by the spotting method. Patent Document 2 discloses a method for manufacturing an array base on which droplets supplied from a micropipette are efficiently arranged and which has a structure effective in preventing the contamination of the droplets.

Patent Document 1: Japanese Unexamined Patent Application Publication No. 2004-045055

Patent Document 2: Japanese Unexamined Patent Application Publication No. 2004-004076

Probe arrays preferably include various types of probes (probes holding different types of probe molecules or probes their selves) arranged in a predetermined area. That is, in the probe arrays, the number of the probes arranged in a unit area is preferably large.

There is a problem in that the spotting method is unsuitable for manufacturing a probe array with a sufficiently high degree of integration because spots of a probe solution spread on a base.

In order to solve the problem, the following techniques have been proposed: a technique in which frames for preventing such spots from expanding on a base are formed and a technique in which the expansion of such spots is prevented in such a manner that a hydrophobic pattern is formed on a base. However, the intervals between the spots are limited to about 150 µm even if these techniques are used.

The probes need to hold a sufficient number of probe molecules. When the number of the probe molecules held by the probes is insufficient, the number of target molecules binding to or hybridizing with the probes is insufficient; hence, it is difficult to detect the target molecules. In a high-integration probe array manufactured by the spotting method, spots have a small area and therefore the number of probe molecules in each spot is insufficient; hence, the ability of this array to detect the target molecules is low.

The number of the probe molecules held by the probes is preferably constant. This is because the number of the target molecules binding to or hybridizing with the probes varies when the number of the probe molecules held by the probes is not constant even if test solutions have the same target concentration. If the number of the target molecules binding to or hybridizing with the probes varies, the intensity of signals varies; hence, the concentration of the target molecules in each test solution cannot be precisely determined. The spotting method has a problem in that the amount of the probe solution spotted onto the base varies. That is, there is a problem in that the number of the probe molecules, which are adsorbed on the base after the probe solution is dried, is likely to vary. In the manufacture of a high-integration probe array, the amount of the probe solution spotted thereonto is very small and therefore the amount of the probe solution differs between the probes. This leads to a problem in that the number of the probe molecules varies significantly.

SUMMARY OF THE INVENTION

It is an object of the present invention to provide a high-integration probe array in which a sufficient number of probe molecules are uniformly held by probe-holding portions and in which the intervals between probes are 100 µm or less. It is an object of the present invention to provide a method for manufacturing the probe array.

In order to solve the above problems, the inventions of the present application are configured as described below.

A probe array base of the invention is characterized in including a solid base member having a principal surface and probe-holding portions arranged on the principal surface of the solid base member in a projecting manner. The probe-holding portions have grooves.

A probe array base of the invention is characterized in that the probe-holding portions project perpendicularly from the principal surface of the solid base member and the grooves extend substantially in parallel to the direction in which the probe-holding portions project.

A probe array base of the invention is characterized in that the inequalities 1 μm≤W≤100 μm and D≥2W hold, where W represents the size of gaps caused in the probe-holding portions by the grooves and D represents the size of the probes that project from the principal surface of the solid base member.

A probe array base of the present invention preferably includes a solid base member having a principal surface and probe-holding portions which are arranged in the principal surface of the solid base member and which have pores. The probe-holding portions have partitions.

A probe array base of the invention is characterized in that the partitions have parts disconnected from the walls of the pores.

A probe array base of the invention is characterized in that the partitions project from the principal surface of the solid base member.

A probe array base of the invention is characterized in that the solid base member and the probe-holding portions are formed as a single piece from the same material.

A probe array base of the invention is characterized in that the solid base member and the probe-holding portions are made of single-crystalline silicon, the principal surface of the solid base member is oriented in the [110] plane, and the probe-holding portions have surfaces which are connected to the principal surface of the solid base member and which are oriented in the [111] plane.

A probe array according of the present invention includes the above-described probe array base. The probe-holding portions are supplied with a probe solution by capillary action.

A method for manufacturing a probe array according to the present invention includes supplying a probe solution to the probe-holding portions by capillary action.

A method for manufacturing the probe array base includes a step of forming an oxide film on a single-crystalline silicon substrate, a step of patterning the oxide film, a step of etching the single-crystalline silicon substrate with an alkali solution using the patterned oxide film as a mask, and a step of removing the oxide film.

A method for manufacturing the probe array of the present invention includes the use of a first to an nth probe solution tank arrays (where n is an integer of two or more) including probe solution tanks which are independent of each other and which are arranged at predetermined intervals is characterized in including a first procedure for supplying the probe solution to the probe-holding portions located at positions corresponding to the sequence of the first tank array and an ith procedure for supplying the probe solution to the probe-holding portions which are unsupplied with the probe solution in any one of the first to (i-1)th procedures (where i is an integer of two to n) and which are located at positions corresponding to the sequence of the ith tank array. These procedures are performed in the order of first to nth.

According to the present invention, a probe solution is supplied to grooves or pores present in probe-holding portions by capillary action. The amount of the probe solution held by each probe-holding portion depends on the wettability of the probe solution to the probe-holding portion, the dimensions of the grooves or the pores, and the viscosity of the probe solution. If the grooves or the pores are uniformly formed in the probe-holding portions so as to have a predetermined size, a predetermined amount of the probe solution is held by the probe-holding portions and a variation in the amount thereof is very small. A variation in the number of probe molecules is also very small. Therefore, a high-precision probe array can be formed.

Since the probe solution hardly spreads on a principal surface of a solid base member, the degree of integration of a probe can be increased.

According to the present invention, a probe array base is made of single-crystalline silicon; hence, the following techniques can be used: micro-fabrication techniques, such as a wet etching process using a chemical solution and a dry etching process, for example, RIE, used in the semiconductor industry. These techniques are effective in forming grooves with a size of about 1 μm; hence, a high-integration probe array with a prove interval of 100 μm or less can be manufactured.

REFERENCE NUMERALS 100 probe array base
101 solid base member
102 probe-holding portions
140 probe array base
141 solid base member
142 probe-holding portions
200 single-crystalline silicon substrate 201 silicon dioxide layers
202 photoresist
210 probe-holding pillars
211 probe-holding pillars
215 grooves
300 tank array
301 tank array base material
302 supply port member
305 tank sections
310 probe solutions
320 tank array
321A to 321D cylinders
330 tank array
331A to 331D cylinders
340 tank array
341A to 341D cylinders
400 glass slide
401 probe solution spots

DETAILED DESCRIPTION OF THE INVENTION

Figure 1:
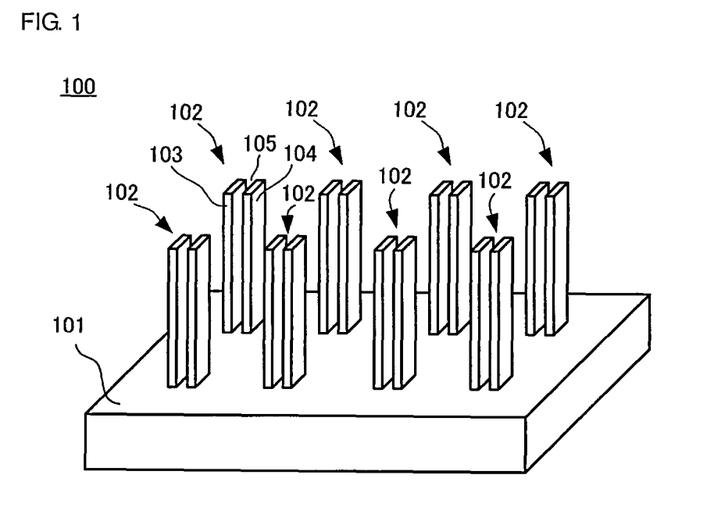
FIG. 1 is a perspective view of a probe array base used to describe a first embodiment of the present invention.

Embodiments of the present invention will now be described with reference to the accompanying drawings. FIG. 1 is a perspective view of a probe array base 100 according to a first embodiment of the present invention. Probe-holding portions 102 are arranged on a solid base member 101 at equal intervals. The probe-holding portions 102 are substantially perpendicular to a principal surface of the solid base member 101. The term "substantially perpendicular" covers the term "right-angled". The probe-holding portions 102 have grooves 105. The probe-holding portions 102 may be prepared separately from the solid base member 101 and then fixed to the solid base member 101 by bonding or the like. The probe-holding portions 102 and the solid base member 101 are preferably integrated together. In the probe array base 100, the probe-holding portions 102 are arrange in a 2×4 array as shown in FIG. 1. However, only a portion of the probe array base is shown in this figure. In the case where a probe array is used as a DNA or antibody chip, several hundreds to several tens of thousands of the probe-holding portions 102 are arranged on the solid base member 101.

Figure 2:
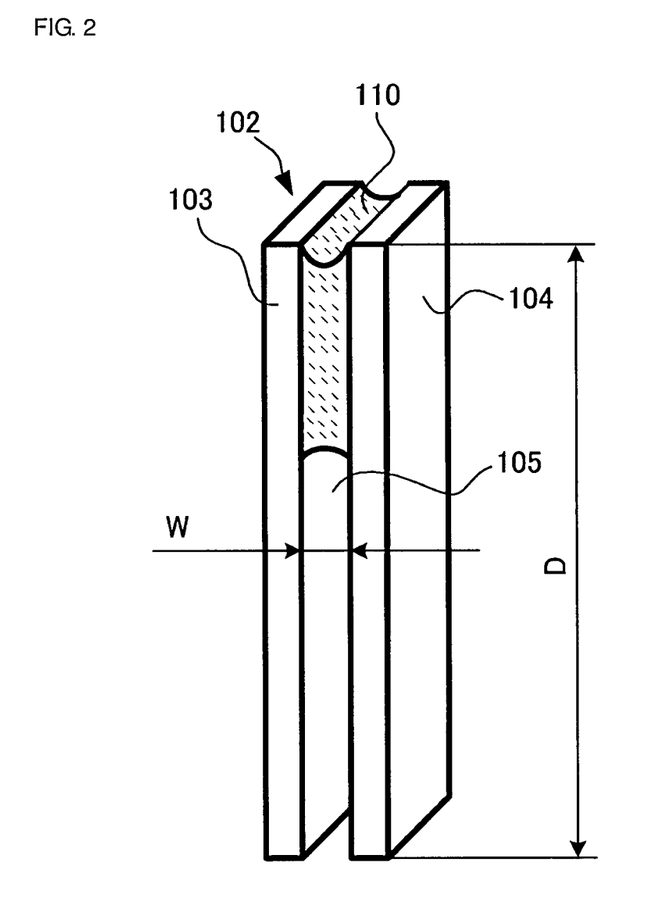
FIG. 2 is an enlarged perspective view illustrating a state where a probe solution is held by a probe-holding portion according to the present invention.

The probe-holding portions 102 are preferably made of a material with high wettability to a probe solution held by the probe-holding portions 102. The probe solution is supplied to the probe-holding portions 102 and then trapped in the grooves 105 by adhesion. The probe solution is trapped in the grooves 105 in the form of a bridge. FIG. 2 shows the probe-holding portions 102 in an enlarged manner. The probe solution 110 is trapped in the grooves 105 of the probe-holding portions 102 in the form of a bridge. When the probe solution 110 is aqueous, the probe-holding portions 102 are preferably hydrophobic except that only surfaces of the probe-holding portions 102 that have the grooves 105 are hydrophilic.

The probe solution 110 can be supplied to the probe-holding portions 102 in such a manner that the tips of the probe-holding portions 102 are brought into contact with the surface of the probe solution 110. When the grooves 105 have a sufficiently small width, the probe solution 110 is drawn into the grooves 105 by capillary action. The drawing of the probe solution 110 into the grooves 105 depends on the adhesion thereof and therefore a certain amount of probe solution 110 is held in the grooves 105. A constant amount of the probe solution can be held by the probe-holding portions 102 by supplying the probe solution 110 as described above.

In order to cause capillary action, the width W of each groove shown in FIG. 2 is preferably small, that is, the groove preferably has a width of 100 μm or less. In order to hold a larger amount of the probe solution, the depth D of the groove is preferably two times greater than that of the width W thereof. Probe-holding pillars 103 and 104 need not necessarily be unequal in height.

The probe solution can be held in the grooves 105 by forcedly injecting the probe solution 110 into the grooves 105 instead of capillary action. In this case, the amount of the probe solution forcedly injected thereinto needs to be constant.

Figure 3:
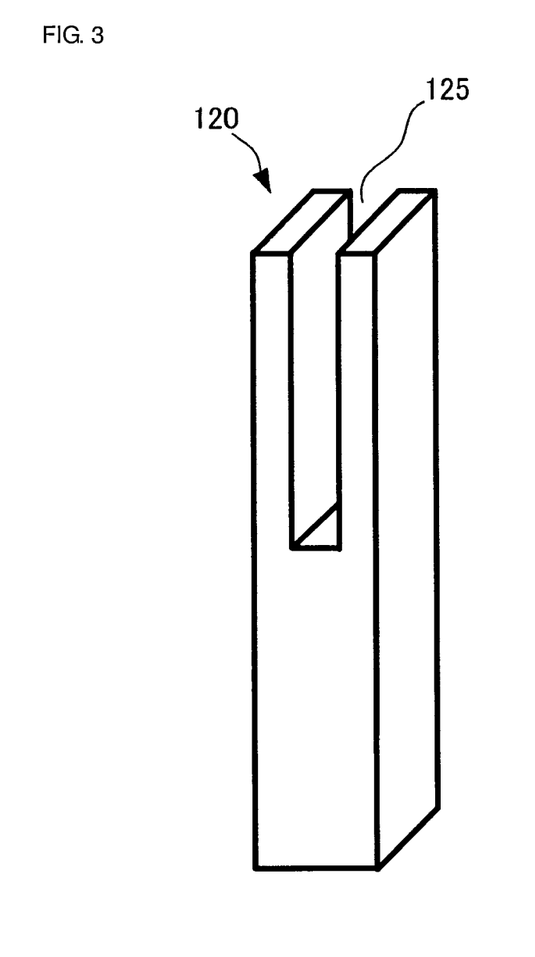
FIG. 3 is an enlarged perspective view of a probe-holding portion used to describe a second embodiment of the present invention.

The shape of the grooves is not limited to one shown in FIG. 2. Modifications thereof are described below with reference to embodiments. FIG. 3 is an enlarged perspective view of one of probe-holding portions 120 according to a second embodiment of the present invention. The probe-holding portions 120, as well as the probe-holding portions 102 described in the first embodiment, are arranged on a solid base member 101. The probe-holding portions 120 each have a groove 125 with a length unequal to that of the probe-holding portions 120. When the depth D of the groove satisfies the inequality D≧2W as described in the first embodiment, the groove 125 may be formed as shown in FIG. 3.

Figure 4:
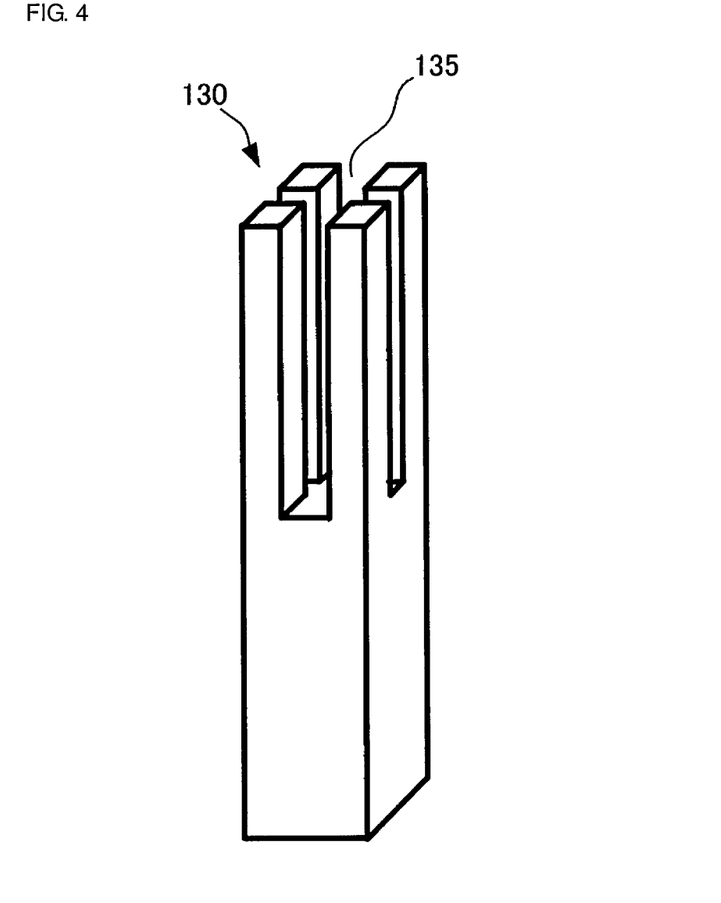
FIG. 4 is an enlarged perspective view of a probe-holding portion used to describe a third embodiment of the present invention.

FIG. 4 is an enlarged perspective view of one of probe-holding portions 130 according to a third embodiment of the present invention. The probe-holding portions 130, as well as the probe-holding portions 102 described in the first embodiment, are arranged on a solid base member 101. The probe-holding portions 130 each has a groove 135 with a cross shape in plan view. This configuration allows the probe-holding portions 130 to hold a larger amount of a probe solution.

Figure 5:
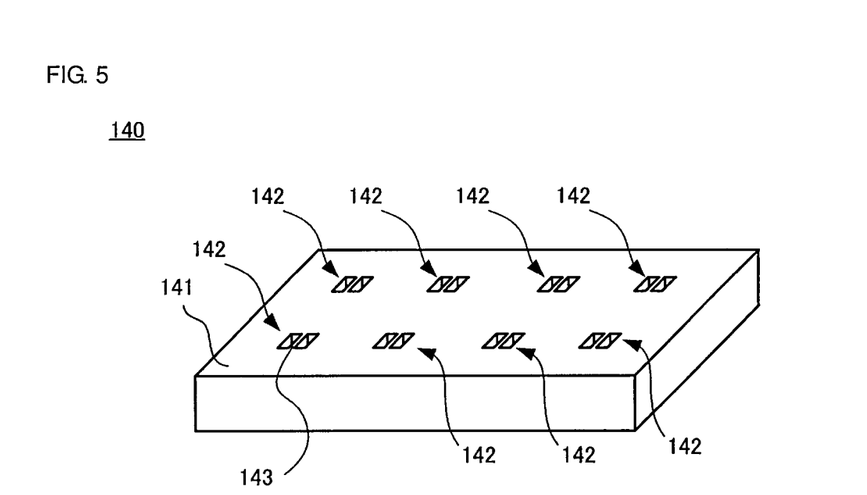
FIG. 5 is a perspective view of a probe array used to describe a fourth embodiment of the present invention.
Figure 6:
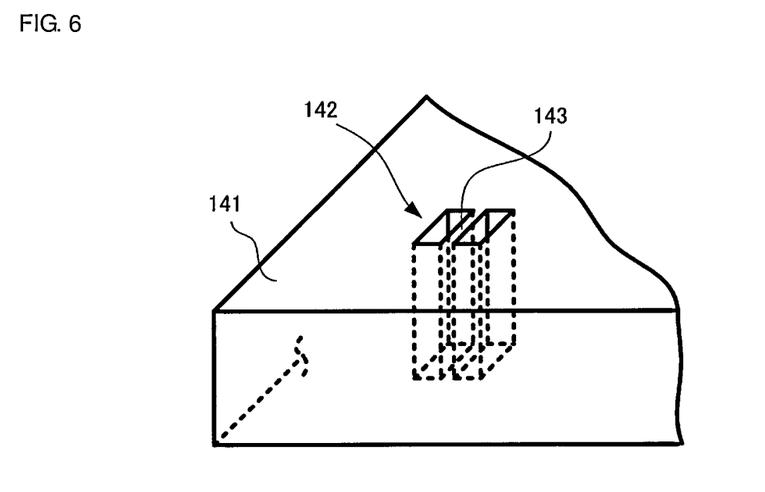
FIG. 6 is an enlarged perspective view of a probe-holding portion used to describe the fourth embodiment of the present invention.

FIG. 5 is a perspective view of a probe array base 140 according to a fourth embodiment of the present invention. Probe-holding portions 142 are arranged in a principal surface of a solid base member 141. The probe-holding portions 142 have pores formed in the principal surface of the solid base member 141. The pores contain partitions 143. The partitions 143 are connected to the walls of the pores. In this embodiment, the pores are completely partitioned. The partitions 143 and the solid base member 141 may be made of the same material or may be formed as a single piece. FIG. 6 is an enlarged perspective view of a portion shown in FIG. 5. The pores of the probe-holding portions 142 reach the bottom surface of the solid base member 141, that is, the pores are perforations. The reason why such perforations are used is that air is readily removed from the probe-holding portions 142 when the probe solution is placed into the probe-holding portions 142. The pores need not necessarily be such perforations. The partitions 143 are necessary to supply the probe solution to the probe-holding portions 142 by capillary action. The operation of the partitions 143 is as described below.

Figure 7:
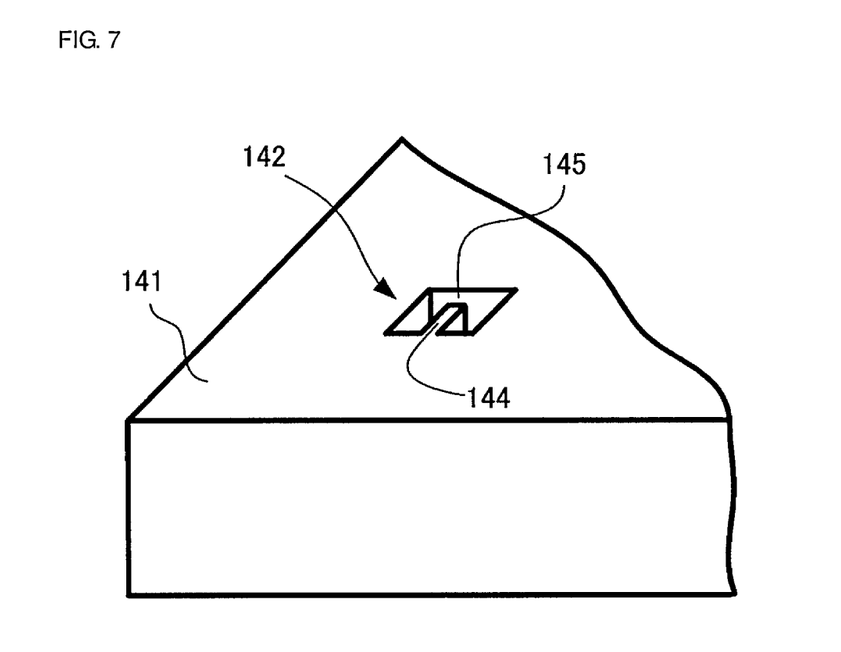
FIG. 7 is an enlarged perspective view of a probe-holding portion used to describe a fifth embodiment of the present invention.

The pores of the probe-holding portions 142 need not necessarily have a rectangular shape in cross section as shown in FIG. 5 and may have a circular shape, an ellipsoidal shape, an elliptical shape, or another shape. The partitions 143 also need not necessarily have such a shape as shown in FIG. 5. A modification thereof is described in an embodiment below. FIG. 7 is a partly enlarged view similar to FIG. 6 and shows a fifth embodiment different in the shape of the partitions 143 from the fourth embodiment. Each partition 144 has a discontinuous part 145 that is partly disconnected from the wall of a pore. If this pore is completely partitioned, this pore has two sub-pores that are substantially independent from each other. The two sub-pores may contain different amounts of a probe solution. This will not cause a serious problem. The probe-holding portions 142 preferably hold a uniform number of probe molecules. The presence of the discontinuous part 145 is effective in preventing such a problem that the two sub-pores contain different amounts of a probe solution. In the fifth embodiment, the partition 144 has the single discontinuous part 145. The partition 144 may have two discontinuous parts. The discontinuous part 145 need not necessarily have the same length as the depth of this pore.

Figure 8:
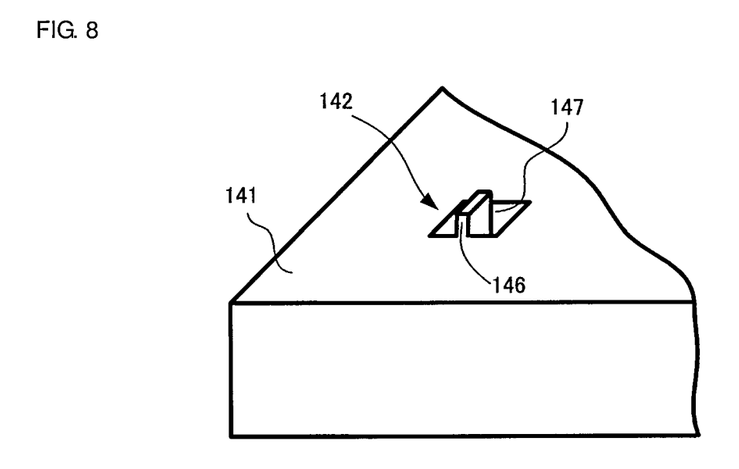
FIG. 8 is an enlarged perspective view of a probe-holding portion used to describe a sixth embodiment of the present invention.

FIG. 8 is a partly enlarged view illustrating a sixth embodiment that is a modification of the fifth embodiment. Each partition 146 projects from a principal surface of a solid base member 141 and has a discontinuous part 147 disconnected from the wall of a pore for forming probe-holding portion 142. Since the partition 146 projects from a principal surface of the solid base member 141, the partition 146 functions as a guide for supplying a probe solution to the probe-holding portion 142. This leads to an improvement in the supply of the probe solution. The operation thereof is as described below.

A method for finely preparing probe-holding portions formed at a high degree of integration will now be described with reference to FIG. 9. A single-crystalline silicon substrate 200 is prepared. The single-crystalline silicon substrate 200 has a thickness of about 0.5 to 1 mm and has principal surfaces (the upper and lower surfaces) oriented in the [110] plane. The principal surfaces of the single-crystalline silicon substrate 200 are oxidized by a steam oxidation process or the like, whereby silicon dioxide layers 201 with a thickness of about 1 μm are formed. FIG. 9(a) shows this situation. FIG. 9(a) is a sectional view of the single-crystalline silicon substrate 200, which has the silicon dioxide layers 201 disposed on the principal surfaces thereof. FIGS. 9(b) to 9(e), as well as FIG. 9(a), are sectional views. In order to show members on a recognizable scale in these figures, different scales are used depending on the size thereof.

Figure 9:
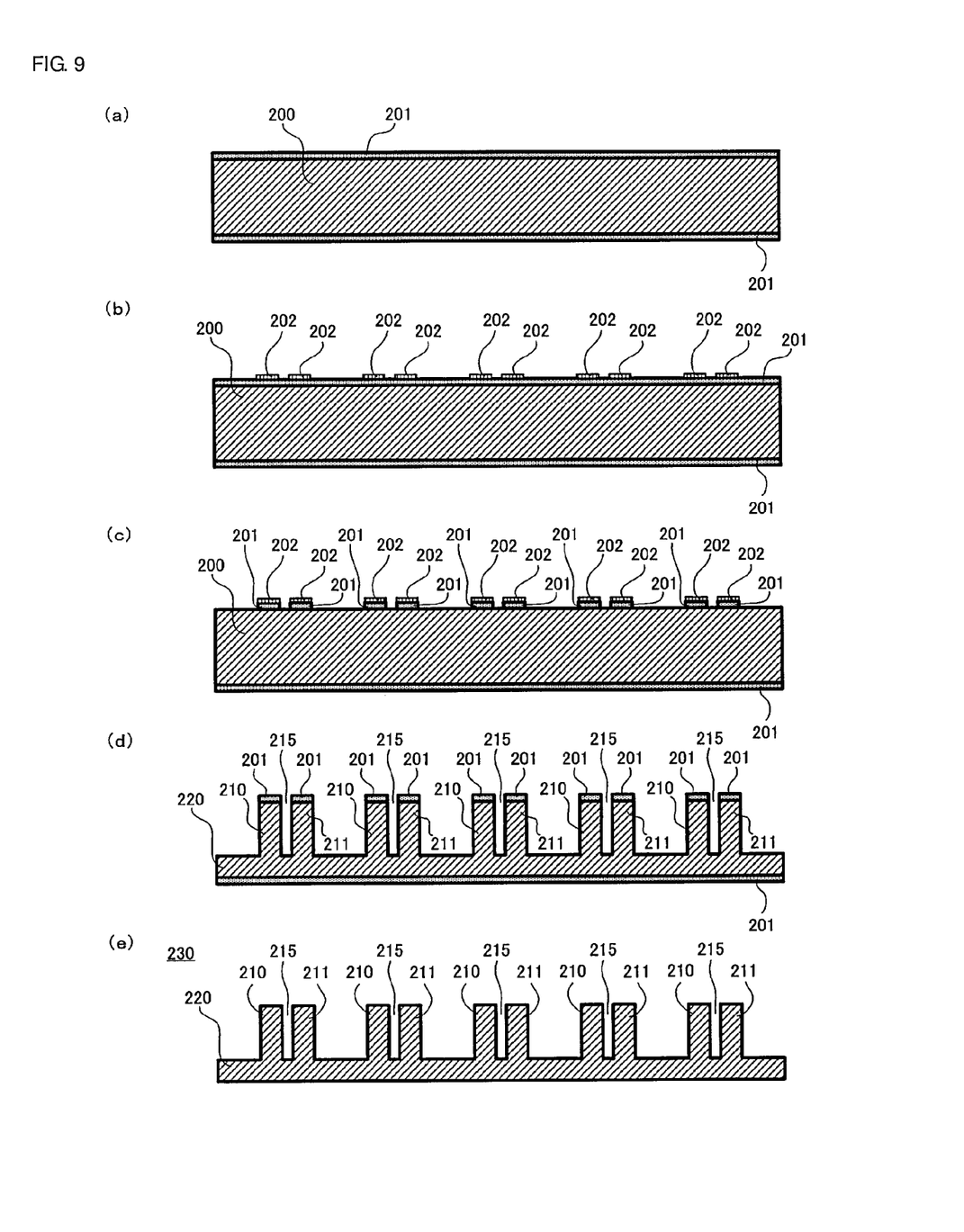
FIG. 9 is an illustration showing a method for manufacturing a probe array base according to the present invention.

As shown in FIG. 9(b), photoresist layers 202 are formed on one of the silicon dioxide layers 201 by patterning. The photoresist layers 202 are used to determine the shape of the etched single-crystalline silicon substrate 200; hence, the photoresist layers 202 are formed by patterning such that two side surfaces of each photoresist layer 202 that are perpendicular to the principal surfaces of the single-crystalline silicon substrate 200 are oriented in the [111] plane.

The silicon dioxide layers 201 are etched such that portions uncovered from the photoresist layers 202 are removed. FIG. 9(c) shows this situation. The silicon dioxide layers 201 can be etched by a wet process using an aqueous solution of hydrofluoric acid or a buffer solution prepared by adding ammonia to such an aqueous solution of hydrofluoric acid, by a dry process using a fluorine-containing gas such as $CF_4$, or another process. In the case where the wet process is used, photoresist layers are formed on the principal surfaces by patterning because the principal surfaces are exposed to an etching solution. In this case, one of the principal surfaces that is not subjected to etching is entirely coated with a photoresist layer.

After the photoresist layers are removed with an organic solvent or the like, the single-crystalline silicon substrate 200 is etched by about 50 μm using the patterned silicon dioxide layer 201 as a mask pattern. FIG. 9(d) shows this situation. An aqueous alkali solution such as an aqueous solution of potassium hydroxide may be used to etch the single-crystalline silicon substrate 200. As a result of the etching of the single-crystalline silicon substrate 200, pairs of probe-holding pillars 210 and 211 are formed such that grooves 215 are present between the probe-holding pillars 210 and 211, whereby probe-holding portions are formed. An unetched portion of the single-crystalline silicon substrate 200 that is not used to form the probe-holding pillars functions as a solid base member 220.

In the case where an alkali solution is used, the etching rate of a [111]-oriented surface (hereinafter referred to as a [111] surface) of the single-crystalline silicon substrate 200 is extremely less than that of a [110]-oriented surface (hereinafter referred to as a [111] surface) thereof. If the grooves are formed so as to have a depth of about 50 μm, the [111] surface is hardly etched. Therefore, the probe-holding portions can be formed without causing a variation in the depth of the grooves.

In final, the silicon dioxide layers 201 are removed with an aqueous solution of hydrofluoric acid and cleaning is then performed, whereby a probe array base 230 is completed. FIG. 9(e) shows this situation. The solid base member 220 shown in FIG. 9(e) corresponds to the solid base member 101, shown in FIG. 1, described in the first embodiment. The probe-holding pillars 210, the probe-holding pillars 211, the grooves 215 correspond to the probe-holding pillars 103, probe-holding pillars 104, grooves 105 described in the first embodiment.

A probe array base manufactured by the method typically includes probe-holding pillars 103 and 104 which each have an upper surface with dimensions of 10 μm×5 μm (a groove 105 is located at a position opposed to each surface with a width of 10 μm) and which have a height of 50 μm, grooves 105 having a width of 5 μm and a depth of 50 μm, and probe-holding portions 102 arranged at a pitch of 80 μm. That is, the probe array base has an extremely high degree of integration and high dimensional accuracy can be achieved. The dimensions of these components are not limited to the above values. Various probe array bases with different dimensions can be obtained by varying the dimensions of photoresist patterns and/or an etching rate.

When the probe array base 230 is used to manufacture a DNA chip, the probe array base 230 is thermally oxidized, whereby oxidation films with a thickness of 100 nm are formed thereon. Surfaces thereof are allowed to react with a silane coupling agent and then an EMCS reagent {N-(6-maleimidocaproloxy)succinimide}, whereby maleimide groups are formed. A probe solution used is a solution containing a DNA with a thiol group. Therefore, both groups react with each other, whereby molecules of the DNA that are probe molecules are held by the probe-holding portions.

The method for manufacturing the probe array base according to any one of the first to third embodiments is as described above. The probe array base according to the fourth or fifth embodiment can be manufactured by a process similar to the method. In this case, a photoresist pattern and/or an etching time may be varied as required.

A technique for allowing the probe-holding portions 102 of the probe array base 100 which is described in one of the first to third embodiments and which has a high degree of integration to hold different probe solutions will now be described with reference to FIGS. 10 to 12.

Figure 10:
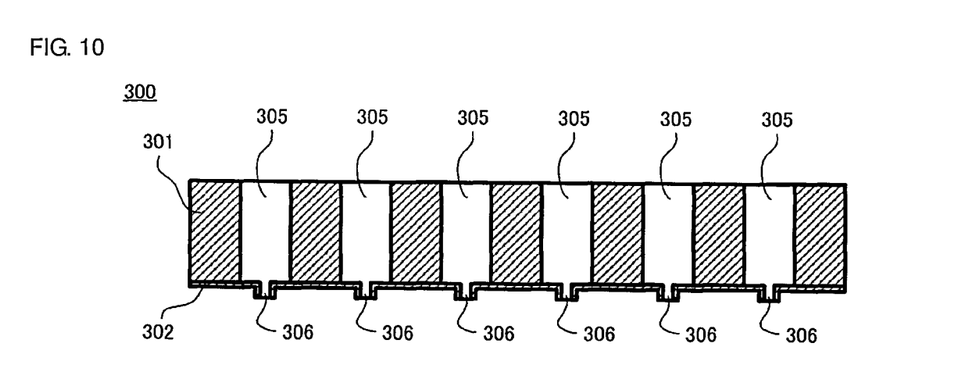
FIG. 10 is a sectional view of a tank array for supplying probe solutions to a probe array base according to the present invention.
Figure 11:
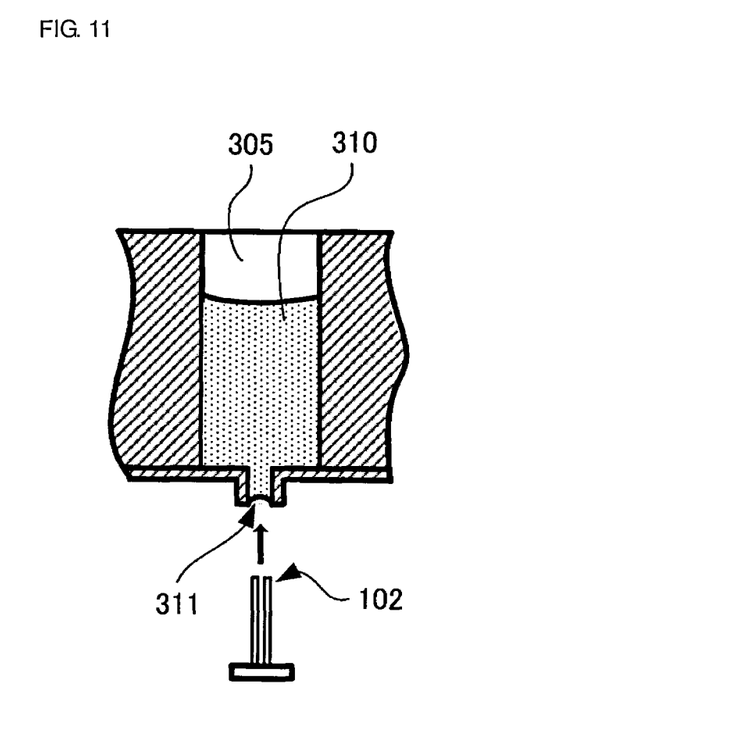
FIG. 11 is a partly enlarged sectional view of a tank array for supplying probe solutions to a probe array base according to the present invention and shows a state where the probe solutions are supplied to probe array base.

FIG. 10 is a sectional view of tank sections 305 of a tank array 300 that is a supplier for supplying the probe solutions to the probe array base 100. The tank array 300 includes a tank array base material 301 and supply port member 302 that have been separately prepared and then bonded to each other. The tank sections 305 are periodically arranged in the tank array base material 301. The supply port member 302 has supply ports 306, periodically arranged, for discharging liquids stored in the tank sections 305.

The tank array can be manufactured by a method similar to the method for manufacturing the probe array base. In particular, the tank array can be manufactured so as to have high dimensional accuracy and a high degree of integration in such a manner that a single-crystalline silicon substrate is etched as described above with reference to FIG. 9. The tank array can be readily manufactured at low cost in such a manner that the tank array base material 301 and the supply port member 302 are separately prepared and then bonded to each other. The tank array base material 301 and the supply port member 302 may be formed as a single piece.

The tank sections 305 contain the probe solutions, which have different characteristics. The probe solutions are supplied to the probe-holding portions of the probe array base through the supply ports 306. FIG. 11 is a partly enlarged view of the tank array shown in FIG. 10 and shows a state where the probe solutions 310 are stored in the tank sections 305. The tank sections 305 and the supply ports 306 have sufficiently small dimensions; hence, the solutions stored in the tank sections 305 are prevented from leaking through the supply ports 306. The surface 311 of the probe solution in each supply port 306 has a shape shown in FIG. 11 because of the surface tension of the probe solution.

The top end of one of the probe-holding portions 102 is inserted into the supply port 306 so as to contact the probe solution surface 311. This allows the probe solution 310 to be held in a groove present in the probe-holding portion 102, whereby a probe is obtained. A state where the probe solution 310 is held by the probe-holding portion 102 is as shown in FIG. 2. The contact of the top end of the probe-holding portion 102 with the probe solution surface 311 allows the probe solution 310 to be drawn into the groove 105 by capillary action.

When the intervals between the tank sections 305 and the intervals between the supply ports 306 are equal to the intervals between the probe-holding portions of the probe array base, the probe solutions can be supplied to all the probe-holding portions in one operation. However, it is very difficult to adjust the intervals of the tank array to the intervals of the probe array base. In usual, the tank array 300 is formed so as to satisfy the equation Y=nX, wherein n represents an integer of two or more, Y represents the intervals between the tank sections 305 and those between the supply ports 306, and X represents the intervals between the probe-holding portions 102 of the probe array base 100. Other tank arrays 300 having the same intervals Y as those above are prepared. The probe solutions are then sequentially supplied to the probe array base. This procedure is described below.

Figure 12:
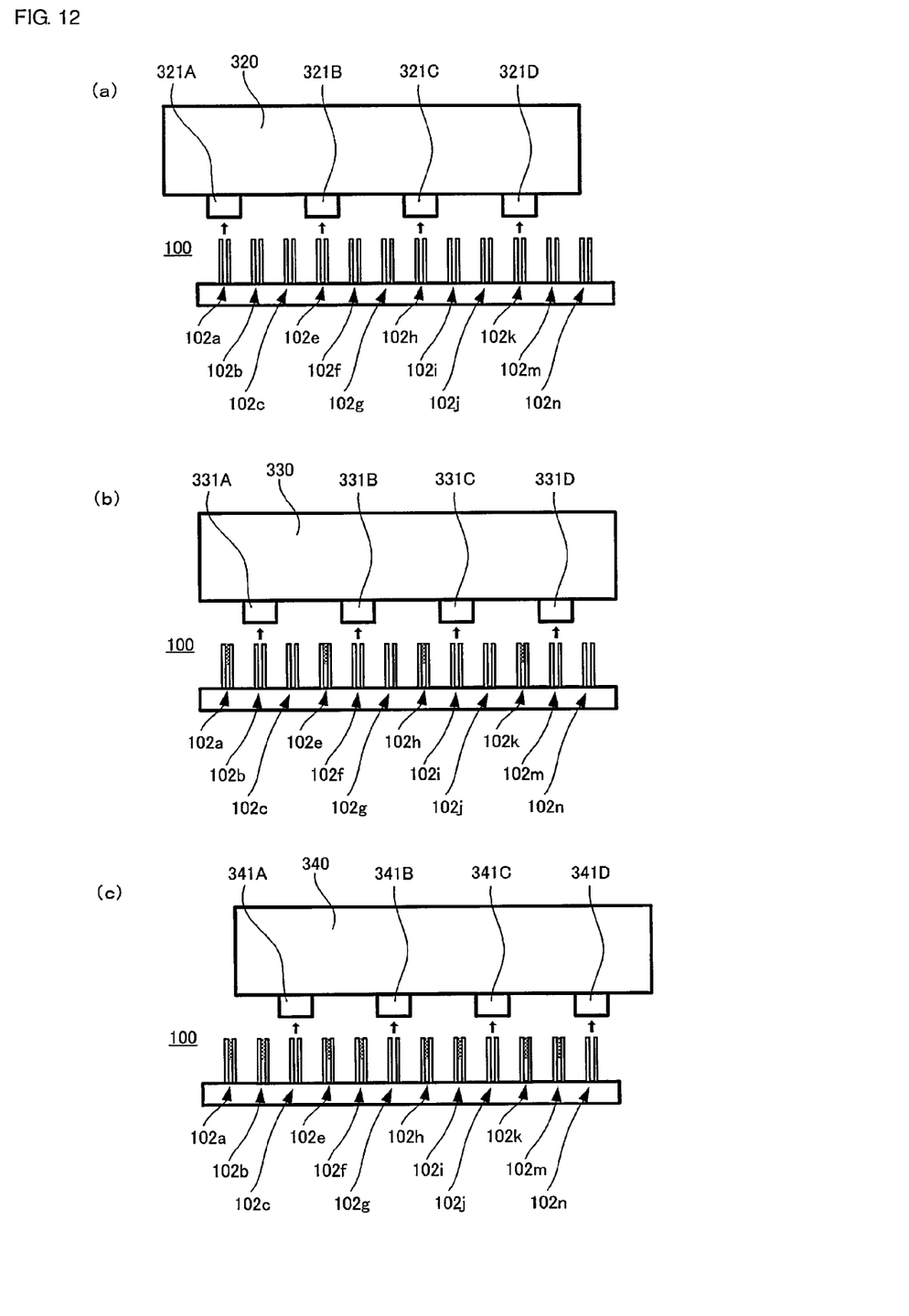
FIG. 12 is an illustration showing a technique for supplying different types of probe solutions to a probe array base according to the present invention.

FIG. 12 includes schematic views showing steps of supplying probe solutions to probe array bases using a plurality of tank arrays. FIGS. 12(a), 12(b), and 12(c) show a tank array 320, a tank array 330, and a tank array 340, respectively, the tank arrays 320 to 340 being different from each other. Probe solutions containing probe molecules different in nature from each other are stored in tanks communicatively connected to supply ports arranged in these tank arrays. The supply ports are arranged in cylinders 321A to 321 D, 331A to 331 D, and 341A to 341 D as shown in FIG. 10.

The cylinders 321A to 321 D, 331A to 331 D, and 341A to 341 D are arranged at equal intervals Y and satisfy the equation Y=3×, wherein X represents the intervals between probe-holding portions 102a to 102n of a probe array base 100. The use of the three tank arrays is described herein. The number of tank arrays used and/or the intervals between tank arrays may be arbitrarily determined. In the case where one or more tank arrays are used, the equation Y=NX may hold, wherein N represents the number of the tank arrays.

FIG. 12(a) is an illustration showing a first sub-step of a step of supplying the probe solutions. Probe-holding portions 102a, 102e, 102h, and 102k of the probe array base 100 are simultaneously inserted into the cylinders 321A to 321 D of the tank array 320, whereby the probe solutions are supplied to these probe-holding portions. The length of inserted parts of these probe-holding portions may be determined such that the top end of each probe-holding portion contacts the surface of the probe solution in each supply port as described above with reference to FIG. 11. This applies to sub-steps below.

FIG. 12(b) is an illustration showing a second sub-step of the probe solution-supplying step. Probe-holding portions 102b, 102f, 102i, and 102m of the probe array base 100 are simultaneously inserted into the cylinders 331A to 331 D of the tank array 320, whereby the probe solutions are supplied to these probe-holding portions.

FIG. 12(c) is an illustration showing a third sub-step of the probe solution-supplying step. Probe-holding portions 102c, 102g, 102j, and 102n of the probe array base 100 are simultaneously inserted into the cylinders 341A to 341 D of the tank array 320, whereby the probe solutions are supplied to these probe-holding portions.

The different probe solutions are supplied to all the probe-holding portions as described above, whereby a probe array is completed. For the sake of clarity, the probe-holding portions are described above on the assumption that the probe-holding portions are arranged in a line. The probe-holding portions may be arranged two-dimensionally on a solid base member. The different probe solutions are stored in the tanks of the tank arrays as described above. The same type of probe solution may be stored in some of the tanks or some of the tanks may contain no probe solution as required.

In order to prepare a probe array having the same sequences of probe solutions, a plurality of probe array bases separate from each other may be prepared and then repeatedly subjected to a step similar to the above step. Alternatively, such a probe array may be manufactured without using such separate probe array bases in such a manner that a probe solution is supplied to groups of some of probe-holding portions from a single tank array; another probe solution is supplied to some of the probe-holding portions, unsupplied with that probe solution, from another tank array; this procedure is repeated such that a plurality of groups including the probe-holding portions having the same probe sequence (the types of probes are the same) are formed on a solid base member; and the solid base member is then divided.

Figure 13:
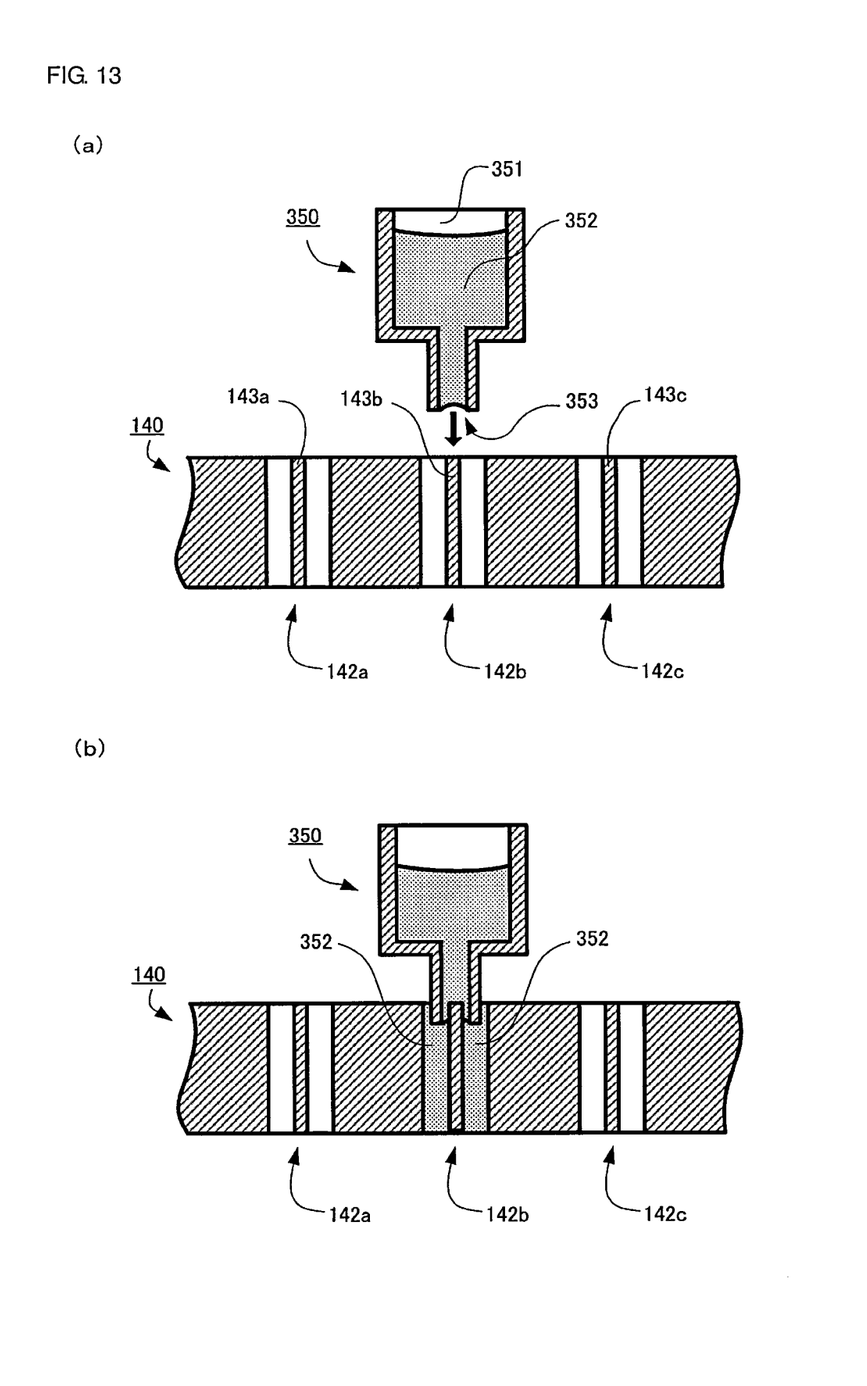
FIG. 13 is an illustration showing a technique for supplying a probe solution to a probe array base according to the fourth or fifth embodiment of the present invention.

A technique for supplying a probe solution to the probe array base described in the fourth or fifth embodiment will now be described. FIG. 13 includes schematic views showing a step of supplying the probe solution to the probe array base. FIGS. 13(a) and 13(b) are sectional views of the probe array base 140 shown in FIG. 5. Probe-holding portions 142a to 142c each correspond to one of the probe-holding portions 142 shown in FIG. 5. The probe-holding portions 142a to 142c have partitions 143a to 143c, respectively. A tank 350 shown in cross section includes a tank section 351 and a supply pair 353. The tank section 351 contains a probe solution 352. Since the tank section 351 and the supply port 353 have sufficiently small dimensions, the solution stored in the tank section 351 is prevented from leaking through the supply pair 353. The tip of the supply pair 353 has a shape similar to that of the tips of probe-holding portions 102 of the probe array base 100 and can be inserted into pores present in the probe-holding portions 142.

FIG. 13(b) shows a state where the supply pair 353 is inserted in the pore of the probe-holding portion 142b. The probe solution 352 held at the tip of the supply pair 353 is drawn into the pore of the probe-holding portion 142b by capillary action, with the partition 143 serving as a guide. The single tank 350 is described above. However, such a tank array shown in FIG. 10 may be used to supply different probe solutions to the probe-holding portions 142 as shown in FIG. 12.

Figure 14:
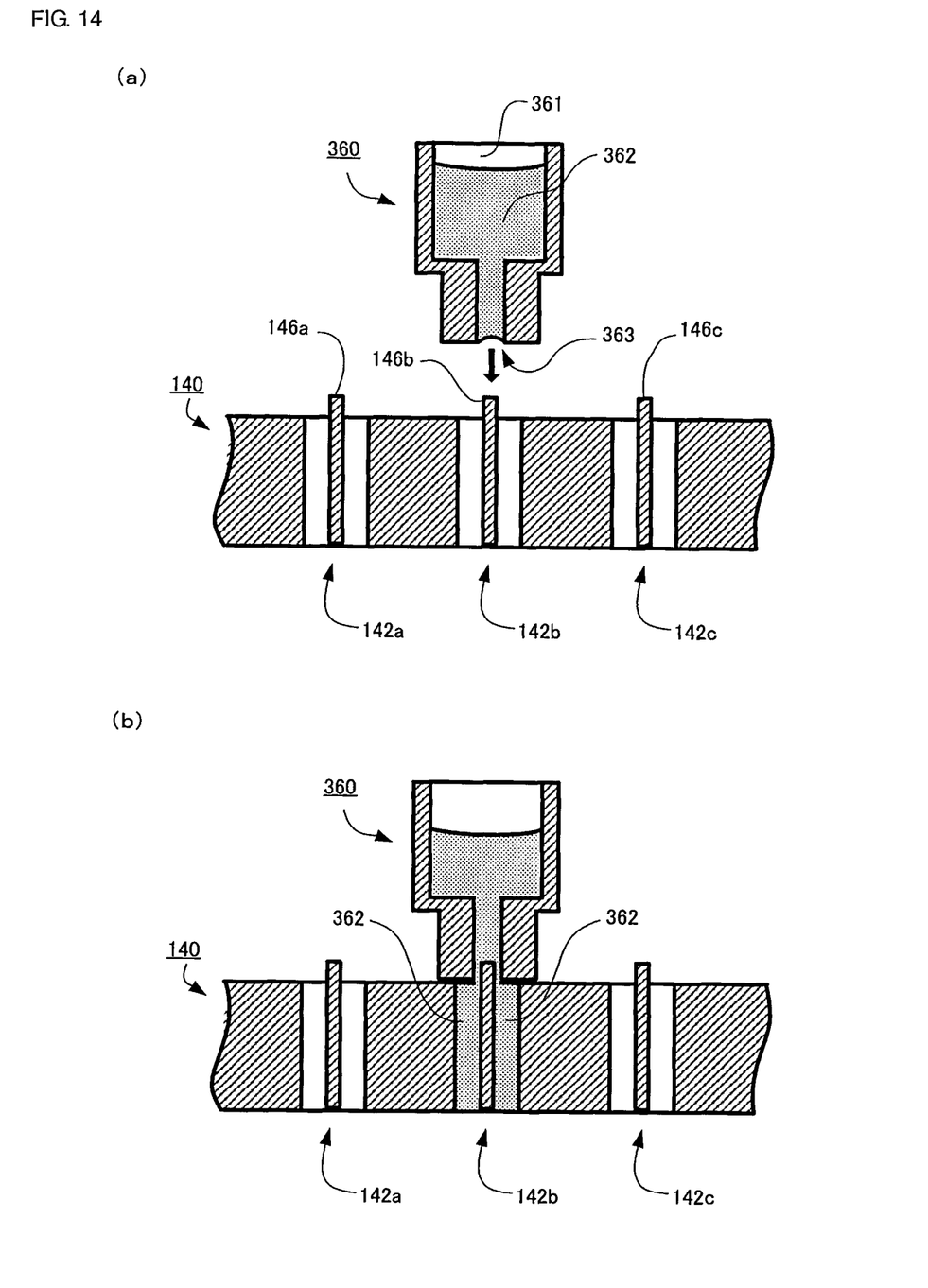
FIG. 14 is an illustration showing a technique for supplying a probe solution to a probe array base according to the sixth embodiment of the present invention.

A technique for supplying a probe solution to the probe array base described in the sixth embodiment will now be described. FIG. 14 includes schematic views showing a step of supplying the probe solution to the probe array base. FIGS. 14(a) and 14(b) are sectional views of the probe array base 140 shown in FIG. 8. Probe-holding portions 142a to 142c each correspond to one of the probe-holding portions 142 shown in FIG. 5. The probe-holding portions 142a to 142c have partitions 146a to 146c, respectively. The partitions 146a to 146c project from a principal surface of a solid base member 141. A tank 360 shown in cross section includes a tank section 361 and a supply port 363. The tank section 361 contains a probe solution 362. Since the tank section 361 and the supply port 363 have sufficiently small dimensions, the solution stored in the tank section 361 is prevented from leaking through the supply port 363. The supply port 363 may have a shape similar to that of the supply pair 353 of the tank 350 shown in FIG. 13 and may be only a pore. This allows the tank 360 to have a simple shape.

FIG. 14(b) shows a state where a projecting portion of the partition 146b is inserted in the supply port 363. The probe solution 362 held at the tip of the supply port 363 is drawn into a pore present in the probe-holding portion 142b by capillary action, with the partition 146b serving as a guide. The single tank 360 is described above. However, such a tank array shown in FIG. 10 may be used to supply different probe solutions to the probe-holding portions 142 as shown in FIG. 12.

The invention claimed is:

1. A probe array base comprising:
   a base member having a principal surface; and
   probe-holding portions which are integral with and arranged in the principal surface of the base member and which have pores,
   wherein the probe-holding portions have vertically arranged partitions, and the partitions are attached to walls of the pores and further wherein the partitions project out from the principal surface of the base member.

2. The probe array base according to claim 1, wherein the partitions have parts disconnected from the walls of the pores.

3. The probe array base according to claim 1, wherein the base member and the probe-holding portions are made of single-crystalline silicon, the principal surface of the base member is oriented in a [110] plane, and the probe-holding portions have surfaces which are connected to the principal surface of the base member and which are oriented in a [111] plane.

4. A probe array comprising the probe array base according to claim 1, wherein the probe-holding portions are supplied with a probe solution by capillary action.

5. A method for manufacturing a probe array including the probe array base according to claim 1, the method comprising supplying a probe solution to the probe-holding portions by capillary action.

6. A method for manufacturing the probe array base according to claim 3, comprising:
   forming an oxide film on a single-crystalline silicon substrate;
   patterning the oxide film;
   etching the single-crystalline silicon substrate with an alkali solution using the patterned oxide film as a mask; and
   removing the oxide film.

7. A method for manufacturing the probe array according to claim 5, wherein the probe solution is supplied to the probe-holding portions by capillary action through a first to an nth position probe solution tank set array, where n is an integer of two or more, the method further comprising:
   a first procedure supplying a probe solution to a first set of the probe-holding portions, the first set of probe-holding portions located at positions corresponding to the positions of the first tank set; and
   an ith procedure supplying the probe solution to an ith set of the probe-holding portions which had been unsupplied with the probe solution in any one of the first to (i−1)th procedures and which are located at positions corresponding to a location of the nth tank set,
   where i is an integer of two to n, and
   wherein the first through ith procedures are performed in the order of first to nth.

* * * * *